US010786300B2

(12) United States Patent
Bazoberry

(10) Patent No.: US 10,786,300 B2
(45) Date of Patent: Sep. 29, 2020

(54) RADIOFREQUENCY DENERVATION NEEDLE AND METHOD

(71) Applicant: Carlos Fernando Bazoberry, Chestnut Hill, MA (US)

(72) Inventor: Carlos Fernando Bazoberry, Chestnut Hill, MA (US)

( * ) Notice: Subject to any disclaimer, the term of this patent is extended or adjusted under 35 U.S.C. 154(b) by 555 days.

(21) Appl. No.: 15/098,213

(22) Filed: Apr. 13, 2016

(65) Prior Publication Data

US 2016/0296275 A1 Oct. 13, 2016

Related U.S. Application Data

(60) Provisional application No. 62/146,560, filed on Apr. 13, 2015.

(51) Int. Cl.
*A61B 18/14* (2006.01)
*A61B 18/00* (2006.01)

(52) U.S. Cl.
CPC .. *A61B 18/1477* (2013.01); *A61B 2018/0044* (2013.01); *A61B 2018/00339* (2013.01); *A61B 2018/00577* (2013.01); *A61B 2018/1432* (2013.01); *A61B 2018/1435* (2013.01)

(58) Field of Classification Search
CPC ........ A61B 18/1477; A61B 2018/1435; A61B 2018/00339; A61B 2018/0044; A61B 2018/00577; A61B 2018/1432; A61M 25/065; A61M 25/06
See application file for complete search history.

(56) References Cited

U.S. PATENT DOCUMENTS

| 4,548,207 A | 10/1985 | Reimels |
| 4,612,934 A | 9/1986 | Borkan |
| 5,191,900 A | 3/1993 | Mishra |
| 5,342,357 A | 8/1994 | Nardella |
| 5,397,338 A | 3/1995 | Grey et al. |
| 5,545,193 A | 8/1996 | Fleischman et al. |

(Continued)

FOREIGN PATENT DOCUMENTS

| EP | 0865768 A1 | 9/1998 |
| EP | 0651661 B1 | 6/2000 |

(Continued)

*Primary Examiner* — Eun Hwa Kim
*Assistant Examiner* — Catherine Premraj
(74) *Attorney, Agent, or Firm* — Thomas P. O'Connell; O'Connell Law Firm

(57) ABSTRACT

A radiofrequency denervation device with a needle and an electrode for actuating an active portion of the needle to produce radiofrequency denervation of the sacroiliac joint. The needle has a tip with an inactive portion and the radiofrequency active portion for producing lesions in surrounding tissue. The active portion and a portion of the inactive portion are disposed in a helical formation concentric with a longitudinal axis of the needle. The helical formation communicates over an arcuate path with an angle of attack. A method of radiofrequency denervation can be performed by rotating the tip of the needle in a screw-like motion in a first rotational direction to achieve a position with the active portion of the tip substantially parallel to a surface of the sacrum and actuating the active portion to produce a lesion. Repositioning and further lesioning can be achieved by selective rotation and actuation of the tip.

11 Claims, 14 Drawing Sheets

(56) References Cited

U.S. PATENT DOCUMENTS

| | | |
|---|---|---|
| 5,609,151 A | 3/1997 | Mulier et al. |
| 5,766,171 A | 6/1998 | Silvestrini |
| 5,776,092 A | 7/1998 | Farin et al. |
| 5,895,386 A | 4/1999 | Odell et al. |
| 5,951,546 A | 9/1999 | Lorentzen |
| 6,002,964 A | 12/1999 | Feler et al. |
| 6,102,886 A | 8/2000 | Lundquist et al. |
| 6,104,957 A | 8/2000 | Alo et al. |
| 6,129,726 A | 10/2000 | Edwards et al. |
| 6,176,857 B1 | 1/2001 | Ashley |
| 6,277,112 B1 | 8/2001 | Underwood et al. |
| 6,280,441 B1 | 8/2001 | Ryan |
| 6,379,349 B1 | 4/2002 | Muller et al. |
| 6,500,173 B2 | 12/2002 | Underwood et al. |
| 6,517,536 B2 | 2/2003 | Hooven et al. |
| 6,562,033 B2 | 5/2003 | Shah et al. |
| 6,620,156 B1 | 9/2003 | Garito et al. |
| 6,692,492 B2 | 2/2004 | Simpson et al. |
| 6,712,811 B2 | 3/2004 | Underwood et al. |
| 6,726,684 B1 | 4/2004 | Woloszko et al. |
| 6,735,474 B1 | 5/2004 | Loeb et al. |
| 6,757,565 B2 | 6/2004 | Sharkey et al. |
| 6,780,181 B2 | 8/2004 | Kroll et al. |
| 6,847,849 B2 | 1/2005 | Mamo et al. |
| 6,869,430 B2 | 3/2005 | Balbierz et al. |
| 6,932,811 B2 | 8/2005 | Hooven et al. |
| 6,974,454 B2 | 12/2005 | Hooven |
| 7,065,412 B2 | 6/2006 | Swoyer et al. |
| 7,097,641 B1 | 8/2006 | Arless et al. |
| 7,169,146 B2 | 1/2007 | Truckai et al. |
| 7,198,626 B2 | 4/2007 | Lee et al. |
| 7,241,292 B2 | 7/2007 | Hooven |
| 7,270,658 B2 | 9/2007 | Woloszko et al. |
| 7,276,063 B2 | 10/2007 | Davison et al. |
| 7,367,973 B2 | 5/2008 | Manzo et al. |
| 7,369,894 B2 | 5/2008 | Gerber |
| 7,393,351 B2 | 7/2008 | Woloszko et al. |
| 7,445,619 B2 | 11/2008 | Auge, II et al. |
| 7,462,178 B2 | 12/2008 | Woloszko et al. |
| 7,771,422 B2 | 8/2010 | Auge, II et al. |
| 7,819,869 B2 | 10/2010 | Godara et al. |
| 7,824,404 B2 | 11/2010 | Godara et al. |
| 8,066,702 B2 | 11/2011 | Rittman, III et al. |
| 8,180,461 B2 | 5/2012 | Mamo et al. |
| 8,260,436 B2 | 9/2012 | Gerber et al. |
| 8,864,759 B2 | 10/2014 | Godara et al. |
| 8,882,755 B2 | 11/2014 | Leung et al. |
| 2002/0049437 A1 | 4/2002 | Silvestrini |
| 2002/0072739 A1 | 6/2002 | Lee et al. |
| 2003/0015707 A1 | 1/2003 | Bosco et al. |
| 2003/0163127 A1* | 8/2003 | Scheib ............... A61B 18/1492 606/41 |
| 2005/0177209 A1 | 8/2005 | Leung et al. |
| 2005/0288730 A1 | 12/2005 | Deem et al. |
| 2006/0020297 A1 | 1/2006 | Gerber et al. |
| 2006/0025763 A1 | 2/2006 | Nelson et al. |
| 2007/0173900 A1* | 7/2007 | Siegel ............... A61B 17/3468 607/41 |
| 2008/0200972 A1* | 8/2008 | Rittman ............. A61B 18/1477 607/117 |
| 2011/0213356 A1 | 9/2011 | Wright et al. |
| 2011/0306851 A1 | 12/2011 | Wang |
| 2012/0004667 A1* | 1/2012 | Reddy ................. A61N 1/0573 606/129 |
| 2012/0116382 A1 | 5/2012 | Ku et al. |
| 2012/0136350 A1* | 5/2012 | Goshgarian ........ A61B 18/1492 606/41 |
| 2013/0012933 A1* | 1/2013 | Pellegrino .......... A61B 17/3472 606/28 |
| 2013/0178910 A1 | 7/2013 | Azamian et al. |
| 2013/0274731 A1* | 10/2013 | Anderson .......... A61B 18/1492 606/33 |
| 2013/0304062 A1 | 11/2013 | Chan et al. |

FOREIGN PATENT DOCUMENTS

| | | |
|---|---|---|
| EP | 1344497 A1 | 9/2003 |
| JP | 2012106081 | 6/2012 |
| JP | 2013540563 | 11/2013 |
| JP | 201439791 | 3/2014 |
| WO | WO8103272 A1 | 11/1981 |
| WO | WO9402077 A2 | 2/1994 |
| WO | WO9422384 A1 | 10/1994 |
| WO | WO9424948 A1 | 11/1994 |
| WO | WO9510318 A1 | 4/1995 |
| WO | WO9510320 A1 | 4/1995 |
| WO | WO9510327 A1 | 7/1996 |
| WO | WO9639967 A1 | 12/1996 |
| WO | WO9706739 A2 | 2/1997 |
| WO | WO9706855 A2 | 2/1997 |
| WO | WO9724074 A1 | 7/1997 |
| WO | WO9819613 A1 | 5/1998 |
| WO | WO9831290 A1 | 7/1998 |
| WO | WO9858747 A1 | 12/1998 |
| WO | WO9942037 A1 | 8/1999 |
| WO | WO9943263 A1 | 9/1999 |
| WO | WO03103522 A1 | 12/2003 |

* cited by examiner

RADIOFREQUENCY DENERVATION NEEDLE AND METHOD

RELATED APPLICATION

This application claims priority to U.S. Provisional Patent Application No. 62/146,560, filed Apr. 13, 2015, which is incorporated herein by reference.

FIELD OF THE INVENTION

The present invention relates generally to pain relief, such as lower back pain relief. More particularly, disclosed herein is a radiofrequency probe needle and a method for using such a radiofrequency probe needle for denervation, such as of the sacroiliac joint.

BACKGROUND OF THE INVENTION

Sacroiliac joint pain is a common cause of chronic low back pain. Indeed, the prevalence of low back pain is reported to be 18%-30%, and sacroiliac joint pain accounts for up to 40% of all low back pain complaints.

The treatment of sacroiliac joint pain is challenging. Treatment options include intra-articular injection of local anesthetic and corticosteroid and surgical stabilization. To date, however, these have not consistently been shown to provide effective and long-term pain relief. The present inventor has appreciated that this is largely a result of the sacrum being complex and variable in shape, particularly along the posterior bone surface.

Radiofrequency denervation of the sacroiliac joint is also commonly employed in seeking to treat sacroiliac joint pain. However, it too produces inconsistent results. The complex and variable sensory supply to the sacroiliac joint is difficult to disrupt completely, which is necessary to successful pain treatment. Consequently, pain can persist, and the treatment itself can be markedly uncomfortable and challenging in view of the need for multiple radiofrequency needles and, additionally or alternatively, the need for driving and maneuvering large and invasive needle structures through significant volumes of tough tissue.

Radiofrequency denervation is designed to be a minimally invasive procedure. When used to treat sacroiliac joint pain, radiofrequency thermal energy is applied to ablate the sensory nerve fibers of the sacroiliac joint. The ablation of the sensory nerve fibers interrupts the nociceptive signals. The ideal method and device must be consistently effective at denervation of the sensory branches emanating from the posterior and lateral surfaces of the S1, S2, and S3 foramens.

Lesions produced under a variety of radiofrequency methods are illustrated in FIG. 5. There, a typical lesion created with a single 18-20G, 10 mm active tip needle using RF current and a single insertion can be seen to be "ovoid" in shape. Such a lesion will normally not exceed 5 mm in diameter with 2-3 mm at the poles and roughly 10 mm in height. This often proves too small in size to be of effective therapeutic benefit if one wants to successfully ablate the sensory nerves emanating from the lateral aspect of the posterior sacral foramen.

As a result, current methods to lesion the sensory nerves 106 emanating from the posterior sacral foramen 104 typically require an array of at least three 18-20G RF needles 108 as shown, for instance, in FIGS. 1 through 4. The needles 108 must be placed perpendicular to the bone 102 of the sacrum 100 just lateral to the lateral foramen 104 with approximately a 3 mm distance between them to create an adequate array of lesions 112. The lesions 112 are established by operation of the RF tip 114 of the needle 108 through an inserted electrode 110. Unfortunately, multiple needle insertions increase the risk of at least one of the placements being in the wrong location and, consequently, the risk that healthy tissue may be undesirably affected while diseased tissue may be left untreated.

Numerous prior art references seek to provide improved methods for treating the sacroiliac region of a patient's body. For instance, U.S. Pat. No. 8,864,759 to Godara et al., which is incorporated herein by reference, is directed to Methods of Treating the Sacroiliac Region of a Patient's Body. There, a longitudinal strip lesion is created by an elongate energy delivery device that is inserted, for example, longitudinally to traverse the intra-articular space of the sacroiliac joint. Energy is then provided to the energy delivery device to create lesioning. Unfortunately, to create lesioning at different levels of tissue, the elongate energy delivery device must be withdrawn and re-inserted thereby increasing discomfort, time, and risk.

With U.S. Pat. No. 8,066,702, which is also incorporated herein by reference, Rittman, III et al. disclose a Combination Electrical Stimulating and Infusion Medical Device and Method that exploits a combined electrical and chemical stimulation lead for treatment of the spine and nervous system. Embodiments are disclosed wherein the stimulation lead has active areas/electrodes separated by insulated or non-conductive areas with the electrodes selectively powered by a radiofrequency generator. A slight curvature can be incorporated along the stimulation lead such that the lead can be inserted lengthwise into a patient's body to achieve denervation. Here too, however, the stimulation lead must be removed and re-inserted to permit secondary lesioning and repositioning.

Such current procedures require increased x-ray exposure, increased operating room time, increased anesthesia time, and requires multiple insertions that are painful for the patient. All this increases the potential damage to the patient, such as where a needle 108 is misplaced and, for example, enters the foramen. Adverse results can include sacral root nerve damage due to direct needle puncture or radiofrequency lesioning of nerves to the lower extremities, bladder, rectum and other pelvic and perineal structures. Traditional RF ablation procedures for the SI joint therefore include several patient risk factors that both patient and physician would prefer to reduce or eliminate.

Although multiple methods have been introduced seeking to relieve lower back pain, there remains a longstanding and recognized need for radiofrequency denervation that reduces or eliminates risk factors to the patient. Due to the shortcomings and disadvantages of existing methods, including current radiofrequency denervation practices as summarized above, the present inventor has appreciated the need for an improved device and method for denervation.

SUMMARY OF THE INVENTION

With a knowledge of the present state of the art, the present inventor set forth with the basic object of providing a method and device that enables effective and reliable denervation of the sacroiliac joint and, potentially, other innervated areas of the body.

An underlying object of embodiments of the invention is to provide a radiofrequency denervation method and device capable of producing larger lesioned areas thereby, in certain practices, treating a greater area of tissue lateral to the posterior sacral foramina and increasing the chance of successfully disrupting the sacral lateral branches.

Another object of embodiments of the invention is to provide a radiofrequency denervation method and device wherein a single, potentially disposable, radiofrequency probe is capable of producing an enlarged lesion size in a precise target area while minimizing or eliminating the burning of tissue that is not involved in the denervation of the sacroiliac joint.

In certain manifestations of the denervation method and device, an object is to permit an operator to locate the active tip of the probe sufficiently parallel to the bone, in front of the lateral aspect of the sacral foramen in a semicircular manner, safely and easily thereby to maximize the chance of complete denervation of the sacroiliac joint.

These and further objects, advantages, and details of the present invention will become obvious not only to one who reviews the present specification and drawings but also to those who have an opportunity to experience an embodiment of denervation method and device disclosed herein in operation. However, it will be appreciated that, although the accomplishment of each of the foregoing objects in a single embodiment of the invention may be possible and indeed preferred, not all embodiments will seek or need to accomplish each and every potential advantage and function. Nonetheless, all such embodiments should be considered within the scope of the present invention.

In carrying forth one or more objects of the invention, an embodiment of the radiofrequency denervation device can be considered to be founded on a needle with a proximal portion and a distal portion. An electrode can engage the needle to provide radiofrequency activation thereto. The needle has a tip with an inactive portion and a radiofrequency active portion capable of producing lesions in surrounding volumes of tissue when rendered active by operation of the electrode. The radiofrequency active portion has at least a portion thereof disposed in a helical formation that communicates over an arcuate path with an angle of attack with a longitudinal dimension and a lateral dimension.

Provided with such a radiofrequency denervation device, a practitioner can undertake a method of radiofrequency denervation within tissue of a patient, such as tissue in proximity to the sacroiliac joint. The method can include inserting the tip of the needle into the tissue of the patient by rotating the tip of the needle in a screw-like motion in a first rotational direction to achieve a tip position within the tissue of the patient. The electrode can be engaged with the needle, and the active portion of the tip can be actuated by the electrode to produce a lesion in the tissue of the patient and concomitant radiofrequency denervation.

Embodiments of the radiofrequency denervation device are contemplated wherein the helical formation of the active portion of the tip of the needle is generally concentric with a longitudinal axis of the needle. It is additionally possible for the distal portion of the inactive portion of the tip of the needle and the active portion of the tip of the needle to be disposed in a generally helical formation. The helical pattern can be consistent in effective diameter, or it could taper in effective diameter toward a distal end of the tip of the needle.

Further, the radiofrequency active portion of the tip of the needle can form the most distal end of the tip of the needle. By way of example, it could spans between approximately 90 degrees and approximately 360 degrees of a helical revolution. For instance, the radiofrequency active portion could span approximately 180 degrees of a helical revolution. The pitch of the helical formation could, for instance, be in the range of approximately 3 millimeters.

Where the method is employed in denervation of the sacroiliac joint, the step of inserting the tip of the needle into the tissue of the patient can comprise inserting the tip of the needle into tissue in proximity to the human sacrum, such as with the active portion of the tip substantially parallel to a surface of the sacrum. More particularly, the active portion of the tip could be positioned in proximity to the human sacrum with the active portion of the tip substantially parallel to the lateral aspect of the posterior sacral foramen. In certain practices, proper placement may be facilitated by contacting bone of the sacrum with the tip of the needle.

To achieve further denervation, the method may further include repositioning the tip of the needle within the tissue of the patient and actuating the active portion of the tip to produce a second lesion in the tissue of the patient. Repositioning the tip of the needle could, for example, be undertaken by rotating the tip of the needle in a second rotational direction, such as by approximately 360 degrees, to achieve a second tip position and then actuating the active portion of the tip to produce a lesion in the tissue of the patient by delivering radiofrequency energy from the electrode to the active portion of the tip.

One will appreciate that the foregoing discussion broadly outlines the more important goals and features of the invention to enable a better understanding of the detailed description that follows and to instill a better appreciation of the inventor's contribution to the art. Before any particular embodiment or aspect thereof is explained in detail, it must be made clear that the following details of construction and illustrations of inventive concepts are mere examples of the many possible manifestations of the invention.

DETAILED DESCRIPTION OF PREFERRED EMBODIMENTS

The radiofrequency denervation method and device disclosed herein is subject to a wide variety of embodiments. However, to ensure that one skilled in the art will be able to understand and, in appropriate cases, practice the present invention, certain preferred embodiments of the broader invention revealed herein are described below and shown in the accompanying drawing figures.

Figure 6:
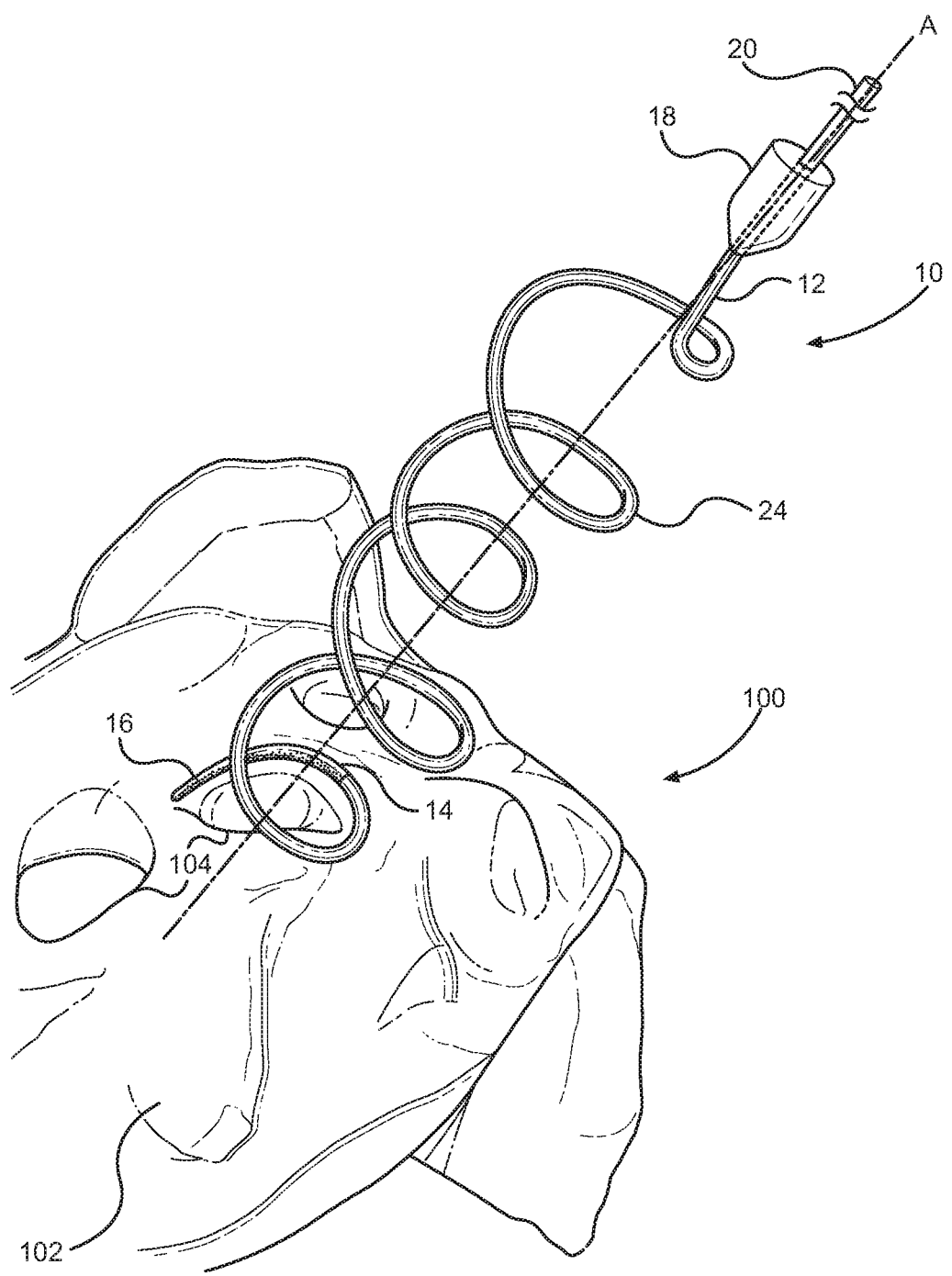
FIG. 6 is a perspective view of a radiofrequency denervation device according to the present invention in a first position during a process of denervation of the sacroiliac joint.
Figure 7:
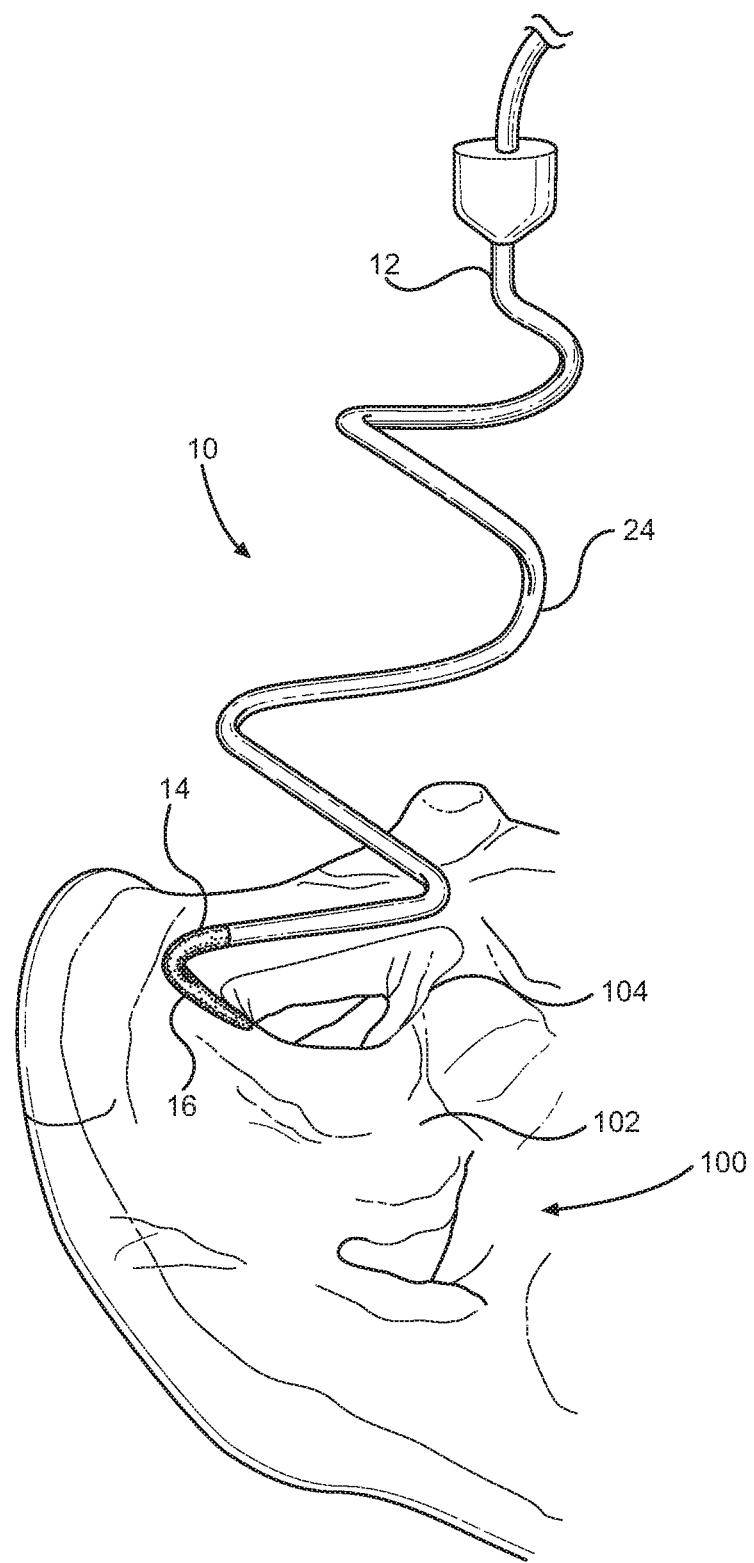
FIG. 7 is a perspective view of the radiofrequency denervation device of FIG. 6 in a second position during a process of denervation of the sacroiliac joint.

A radiofrequency denervation device pursuant to the present invention is indicated generally at 10 in FIG. 6. There, the radiofrequency denervation device 10 is shown during the process of radiofrequency denervation of the sacriliac joint of a patient. The radiofrequency denervation device 10 has a radiofrequency cannula or needle 12 with a proximal portion and a distal portion. A handle 18 is disposed at the proximal portion of an elongate body portion of the needle 12 to enable a manipulation thereof. The needle 12 can be selectively engaged with an electrode 20. The needle 12 has a distal tip 14. The tip 14 has a radiofrequency active area or portion 16 capable of producing lesions in surrounding volumes of tissue when rendered electrically active by operation of the electrode 20. The tip 14 has a non-conductive or inactive area or portion 24 proximal to the active area 16.

Figure 9:
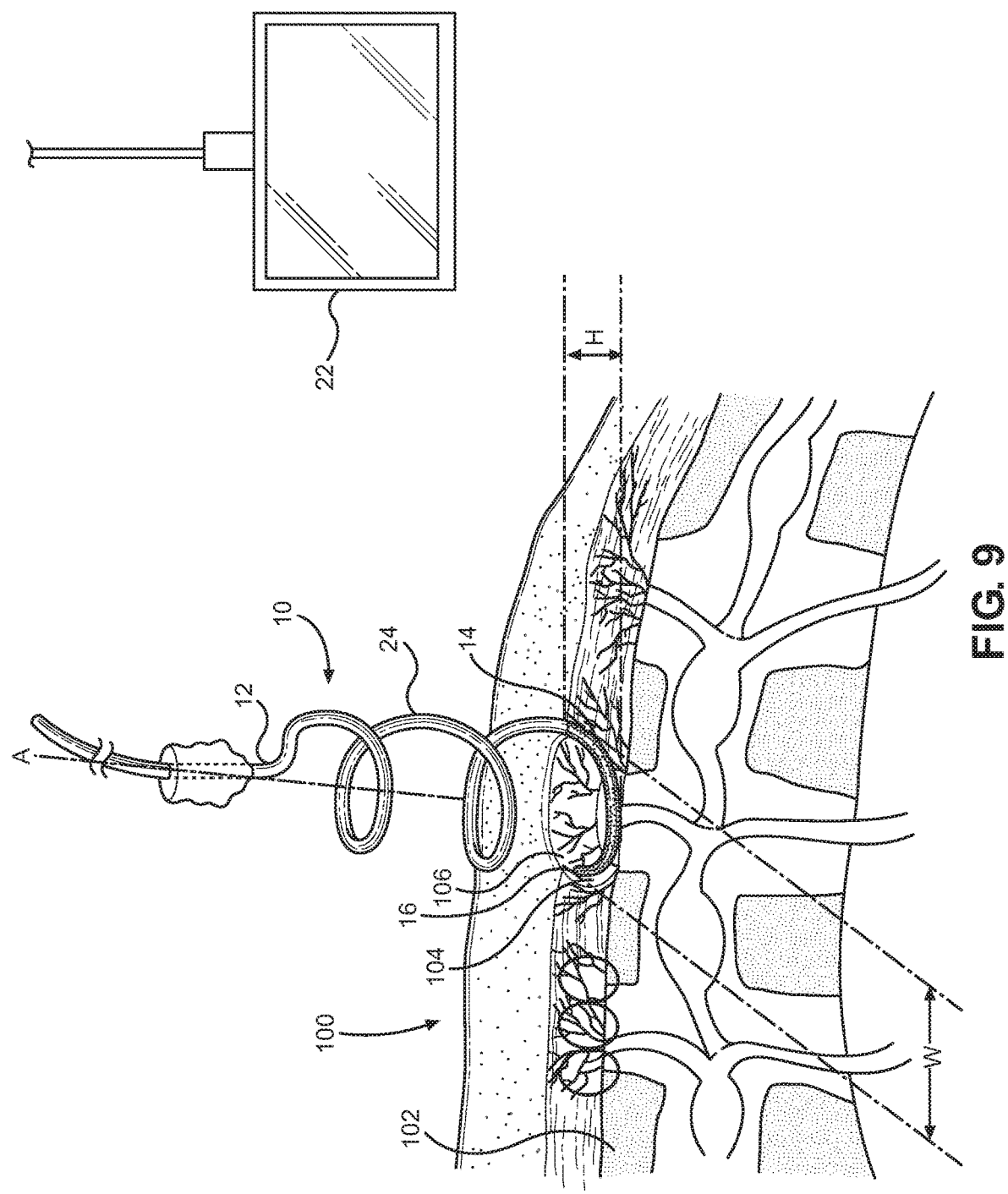
FIG. 9 is a lateral view of a radiofrequency denervation device according to the present invention in a first position during a process of denervation of the sacroiliac joint.
Figure 10:
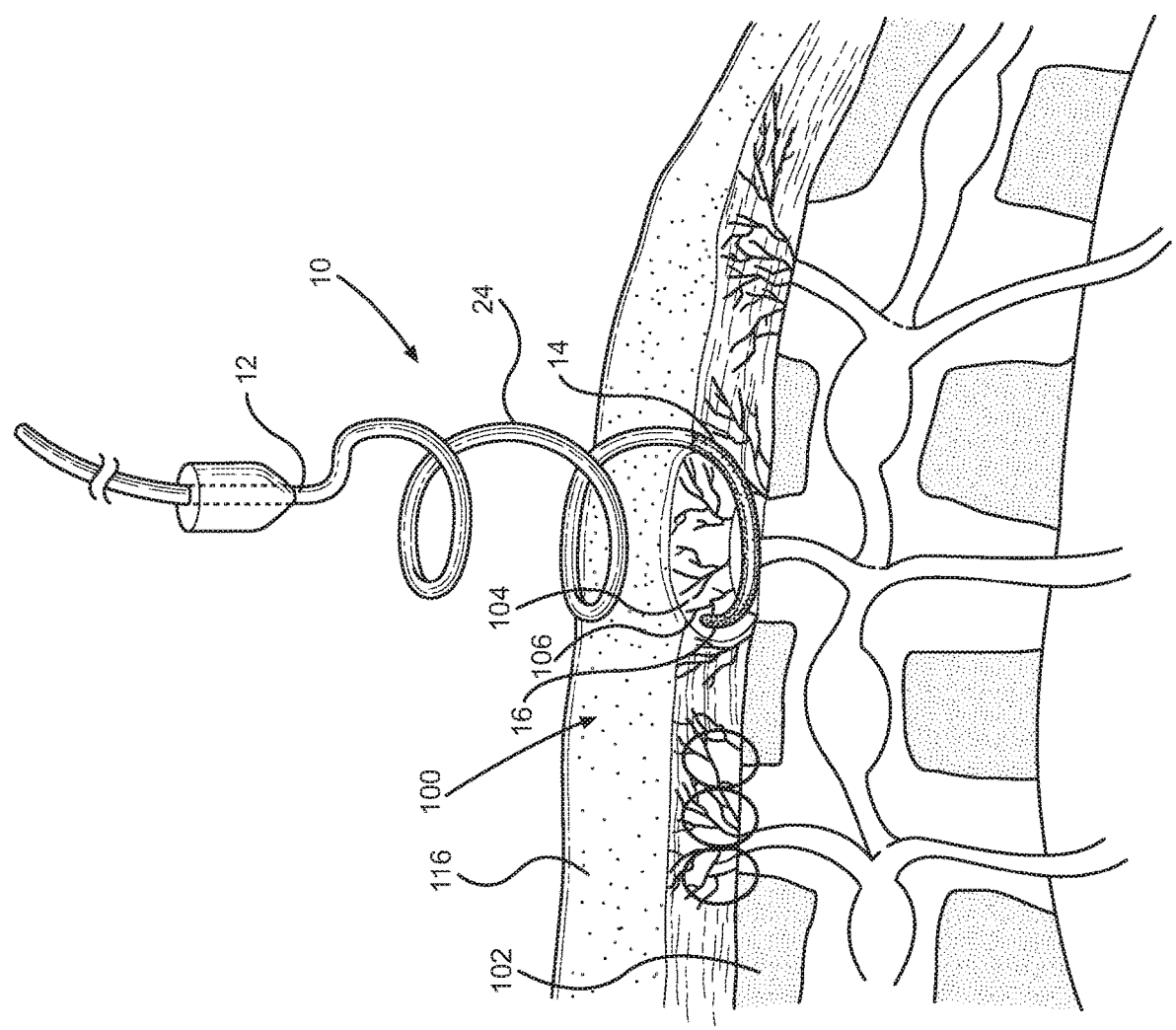
FIG. 10 is a lateral view of the radiofrequency denervation device of FIG. 9 in a second position during a process of denervation of the sacroiliac joint.
Figure 11:
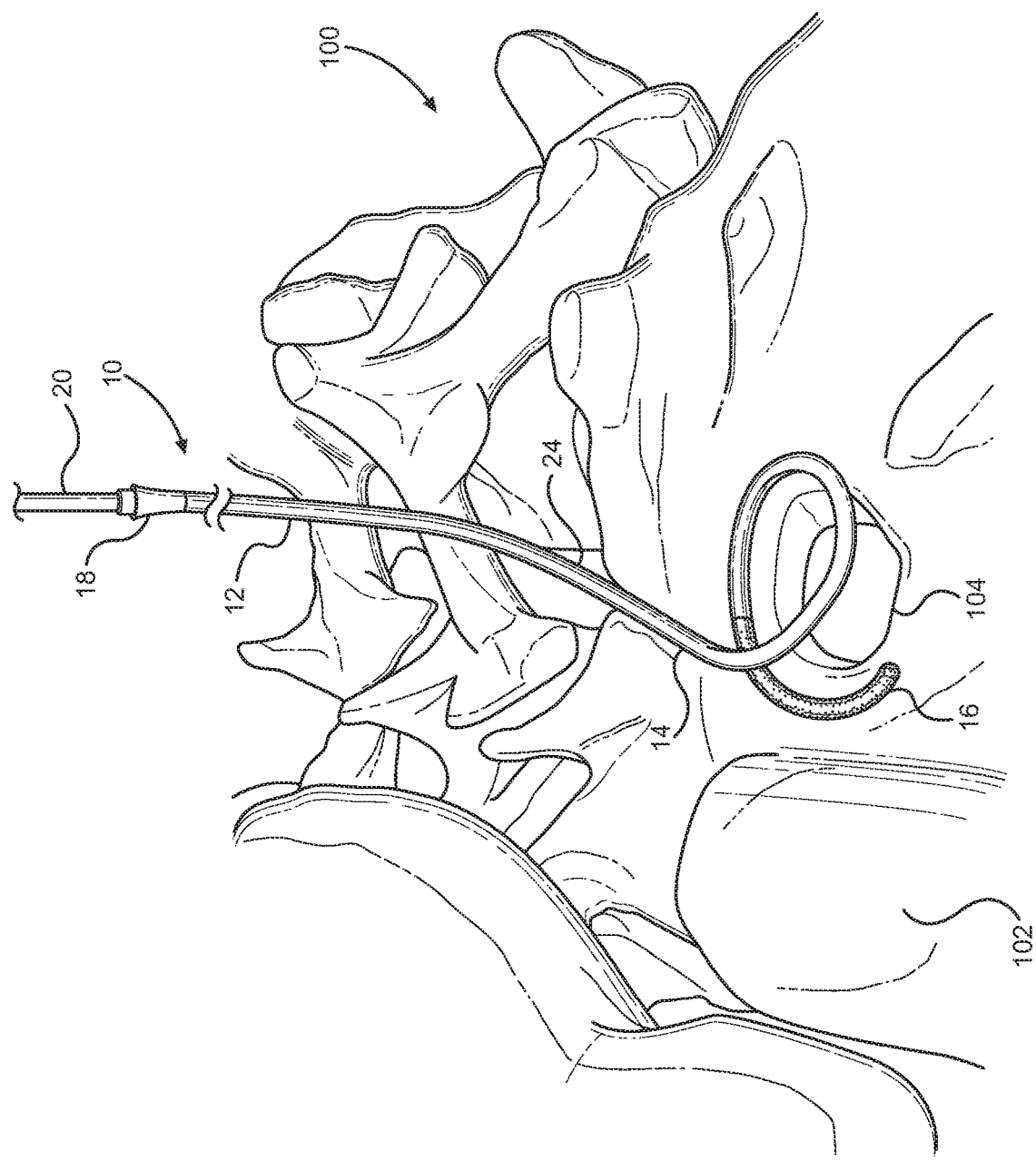
FIG. 11 is a perspective view of a radiofrequency denervation device according to the present invention in a first position during a process of denervation of the sacroiliac joint.
Figure 12:
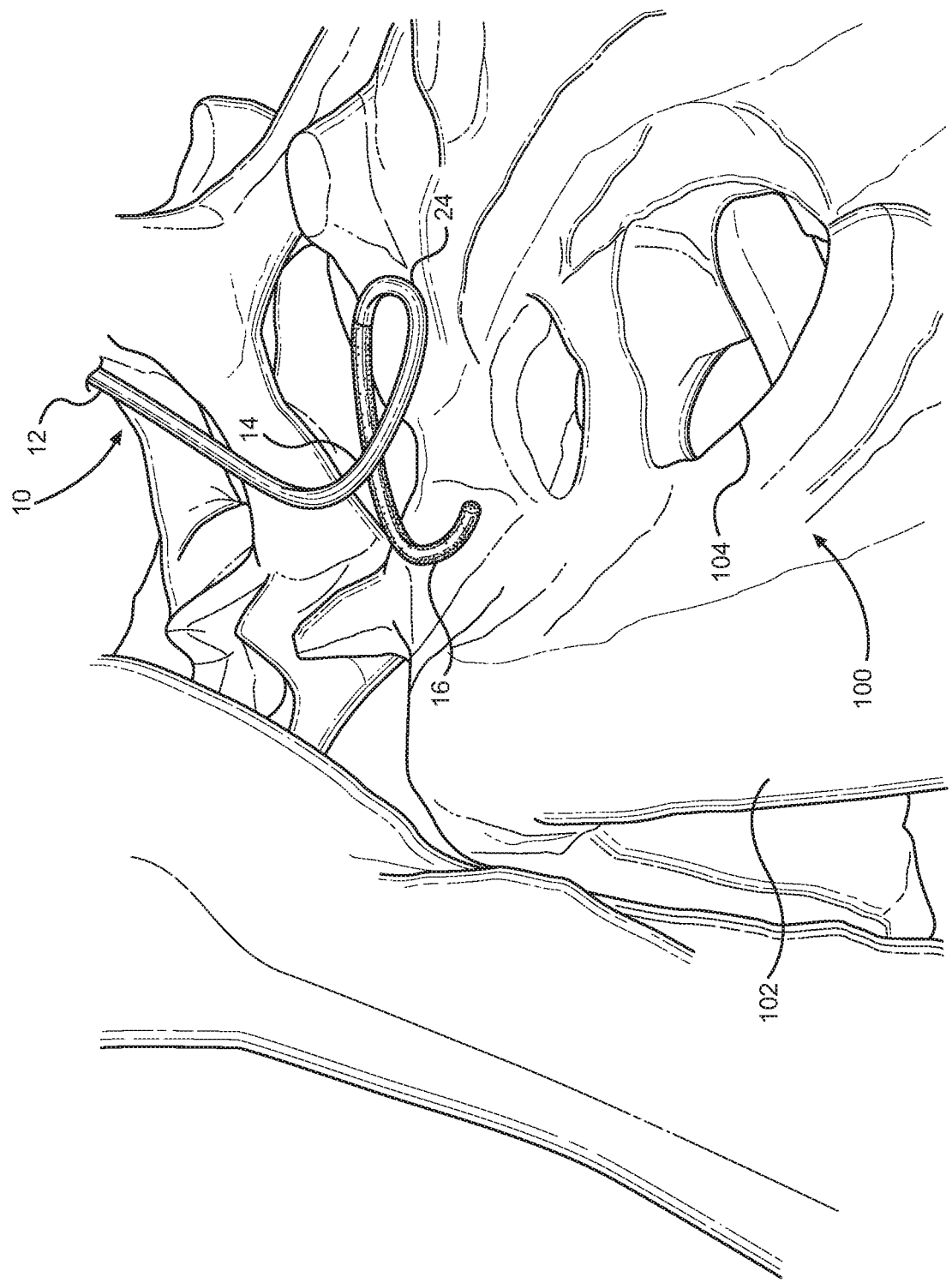
FIG. 12 is a perspective view of the radiofrequency denervation device of FIG. 11 in a second position during a process of denervation of the sacroiliac joint.

The active area 16 can have at least a portion thereof having an arcuate formation. The arcuate formation of the active area 16 of the tip 14 can be generally concentric with a longitudinal axis A of the needle 12. Moreover, the arcuate formation of the active area 16 of the tip 14 could communicate over an arcuate path over a longitudinal dimension H relative to the needle 12 as is illustrated in FIG. 9. The arcuate formation of the active area 16 of the tip 14 could also communicate over an arcuate path over a lateral dimension W relative to the needle 12 as is depicted in FIG. 9. For instance, at least the active area 16 of the tip 14 could follow a helical pattern. In certain practices of the invention, as shown in FIG. 6 for instance, a substantial portion of the tip 14, including the active area 16, could pursue a helical pattern.

The helical pattern of the tip 14 could be generally consistent in effective diameter, or it could taper in effective diameter toward the most distal portion thereof as in the embodiment of FIG. 6. The tapering helical pattern of the tip 14 could be similar to a tapering helical pattern of a distal portion of a helical corkscrew, for instance. Under such constructions, the active area 16 of the tip 14 travels over an arcuate pattern with a given pitch relative to the body portion of the needle 12 thereby travelling along an arcuate path over a longitudinal dimension H and a lateral dimension W. While the elongate body portion of the needle 12 is aligned with the longitudinal axis A of the needle 12, the helical active area 16 traverses an arcuate, helical pattern with an angle of attack relative to the longitudinal axis A of the needle 12. With that, the tip 14 of the needle 12 can enter and travel through the tissue of a patient in a screw pattern, potentially along the angle of attack, with the active tip portion 16 having a substantial lateral dimension W, a longitudinal dimension H, and a curvature. Volumes of tissue lesioned by the active tip portion 16 of the tip 14 will similarly tend to have a substantial lateral dimension, a longitudinal dimension, and, potentially, a curvature.

Using a radiofrequency denervation device 10 as taught herein, a practitioner can practice a method of denervation of, for example, the sacroiliac joint. The method comprises a minimally invasive, percutaneous technique wherein the radiofrequency cannula or needle 12 coupled with the radiofrequency electrode 20 permit a practitioner to denerve the sensory nerves 106 of the sacroiliac joint. The radiofrequency needle 12 and the method for using the same could be performed as an ambulatory surgical procedure using superficial local anesthesia and intravenous sedation when necessary.

The electrode 20 can travel substantially the length of the needle 12. For instance, the needle 12 can be hollow, and the electrode 20 and the needle 12 can be introduced together, such as with the electrode 20 communicating inside the hollow needle 12. The needle 12 could, for instance, be formed from an 18-16G needle that can be disposable. The electrode 20 could be introduced after a stylet is removed from the needle 12.

During use, radiofrequency energy is delivered from and concentrated around the electrode 20 thereby generating heat in the surrounding tissue exposed to the active tip portion 16 of the needle 12. The active tip 16 could be a 20 mm semi-circular tip 16. The active tip 16 could form any multiple of spirals or segment of a spiral. It is also within the scope of the invention to have multiple active tip portions 16. In certain practices of the invention, by way of example and not limitation, the active tip 16 could comprise between approximately 90 degrees and 360 degrees of a revolution of the spiral. As is illustrated, for example, the active tip 16 could span approximately 180 degrees of a revolution of the spiral. The active tip 16 could form the most distal portion of the needle 12 as is depicted, or the active tip 16 could in certain embodiments be spaced from the distal portion of the needle.

The radiofrequency needle 12 can be used with cooled radiofrequency, if necessary. Cooling can, for instance, lead to larger lesions because it can remove heat from the tissue adjacent to the electrode tip 16 thus preventing charring of tissue and maintaining a low impedance to allow dissipation of heat to a larger area.

Figure 8:
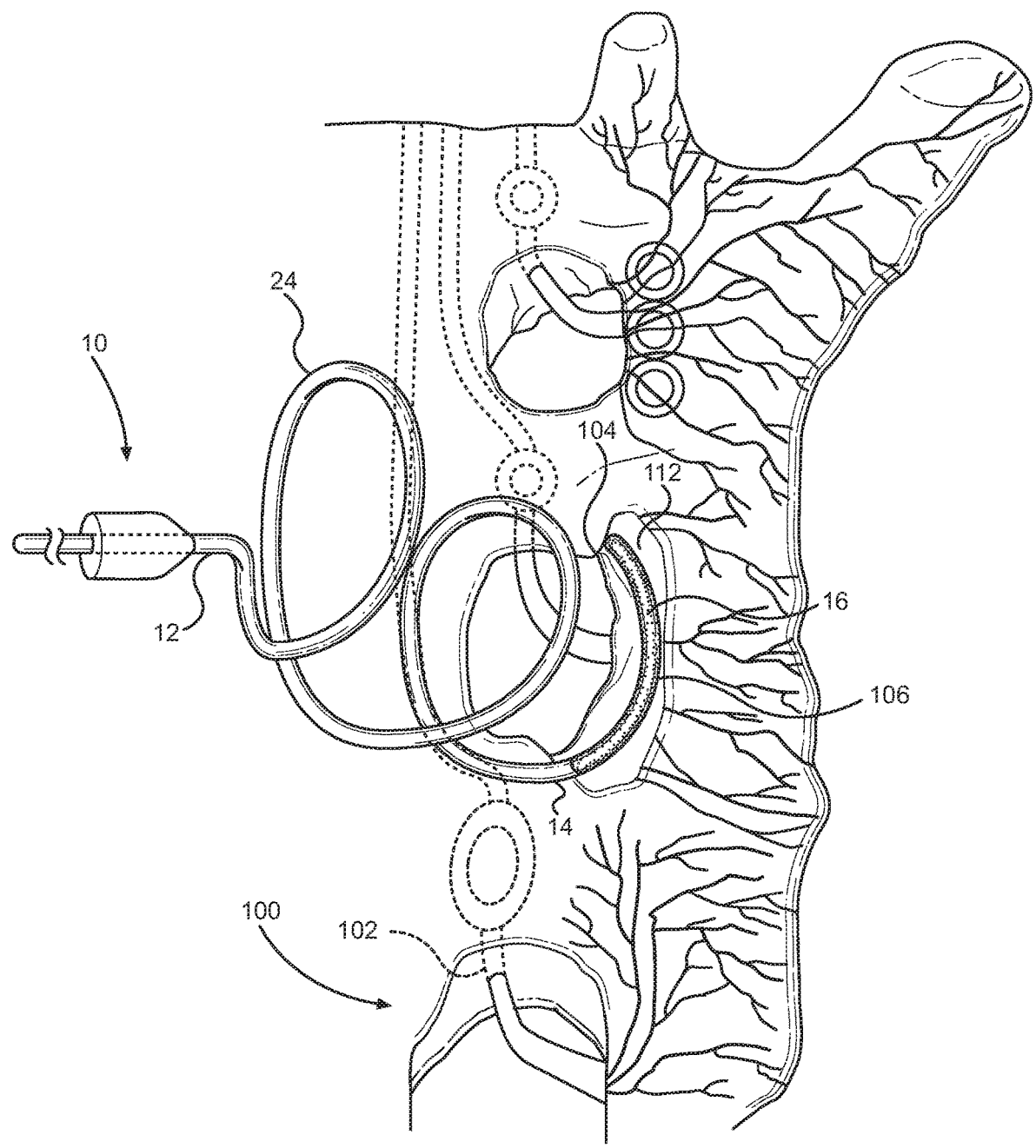
FIG. 8 is a further perspective view of a radiofrequency denervation device pursuant to the invention during a process of denervation of the sacroiliac joint.

As can be perceived by reference to FIGS. 6 and 9, for instance, the active tip 16 can be selectively placed relative to the sacrum 102 or another area of the body. The active tip 16 could, for instance, be disposed to traverse a semicircular pattern spaced, for instance, just a few millimeters parallel to the lateral aspect of the posterior sacral foramen 104 over the bony surface of the sacrum 102. When the tip 16 is activated, radiofrequency heating can effectively denervate the majority, if not all, the sensory branches 106 that leave the foramen 104 over the level of the active tip 16. The needle 12 can have a gauge, such as 18G, sufficient to permit the operator to navigate easily through the patient's tissue 116 as in FIG. 9 to enable the precise positioning of the active tip 16 communicating laterally across the lateral aspect of the posterior sacral foramen 104. Depending on the longitudinal dimension H of the active tip 16 and the positioning of the active tip 16, the active tip 16 can be disposed substantially parallel to the lateral aspect of the posterior sacral foramen 104 with the active tip 16 travelling over the lateral dimension W along the arcuate path of the helical shape of the active tip 16. As seen in FIG. 8, for example, the arcuate active tip 16 positioned substantially parallel to the lateral aspect of the posterior sacral foramen 104 will thus tend to produce a lesion 112 traversing a substantial lateral, arcuate dimension thereby providing a high likelihood of effective denervation of nerves 106 spaced over a given area.

Once an initial placement and lesioning is done, such as described immediately above, the needle 12 can be rotated to adjust the position of the active tip 16, if necessary. Positioning of the active tip 16 and the needle 12 in general can be guided, potentially, through a lateral x-ray view. For instance, depending on whether the helical pattern of the tip 14 is right-handed or left-handed, a clockwise or counter-clockwise rotation of the needle 12 will tend to move the active tip 16 away from the foramen 104. A rotation of the needle 12 over 360 degrees will cause the active tip 16 to be positioned above the previous lesioning.

In one example of the invention, the pitch of the helical tip 14 could be 3 millimeters. With that, the active tip 16, once rotated 360 degrees, would be in a position approximately 10 mm above the previous lesioning. The operator could then rotate the needle 12, such as clockwise or counter-clockwise depending on the pitch of the needle 12, 360 degrees opposite in rotational direction to the first rotational adjustment that placed the active tip 16 originally. As this rotation is undertaken, however, the practitioner could manipulate the needle 12 to adjust the active tip 16 to be approximately 4-5 mm above the first lesion. For a second lesion above the first lesion, the practitioner could, for example, reintroduce the needle 12 clockwise in the embodiment illustrated, manipulating it with slight pulls and pushes to cause the active tip 16 to be positioned, for instance, 4-5 mm above the first lesion. This would add more lesioning to denervate additional sensory branches 106 that might depart from the lateral sacral foramen 104 and travel just above the bony surface 102 of the sacrum 100. Any nerves 106 missed by the initial lesioning within range of the active tip 16 can thus be lesioned.

Where the needle 12 has a large enough gauge, such as 18G by way of example and not limitation, an adequate size lesion can be created for effective denervation without undue damage to surrounding healthy tissues during introduction to the targeted area or during the radiofrequency lesioning. It will further be appreciated that the disclosed helical tip 14 and the overall configuration of the tip 14 of the needle 12 presents a wide enough diameter to make it less apt to enter the sacral foramen 104, which can be dangerous and ineffective in denervation, but small enough to be close to the lateral half sacral foramen 104 in a semicircular configuration.

Figure 1:
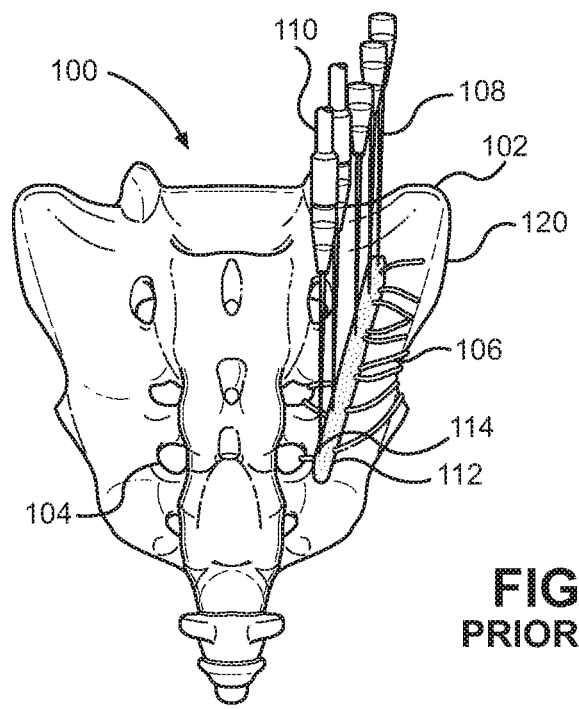
FIG. 1 is a dorsal view of a sacrum during radiofrequency denervation according to the prior art.
Figure 2:
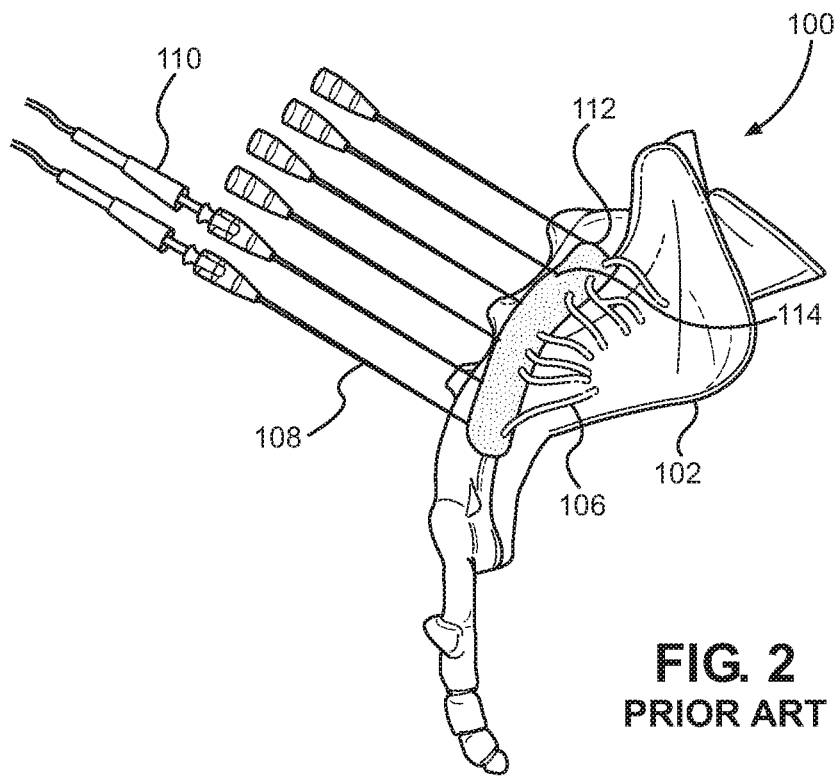
FIG. 2 is a lateral view of the sacrum during radiofrequency denervation, again according to the prior art.
Figure 3:
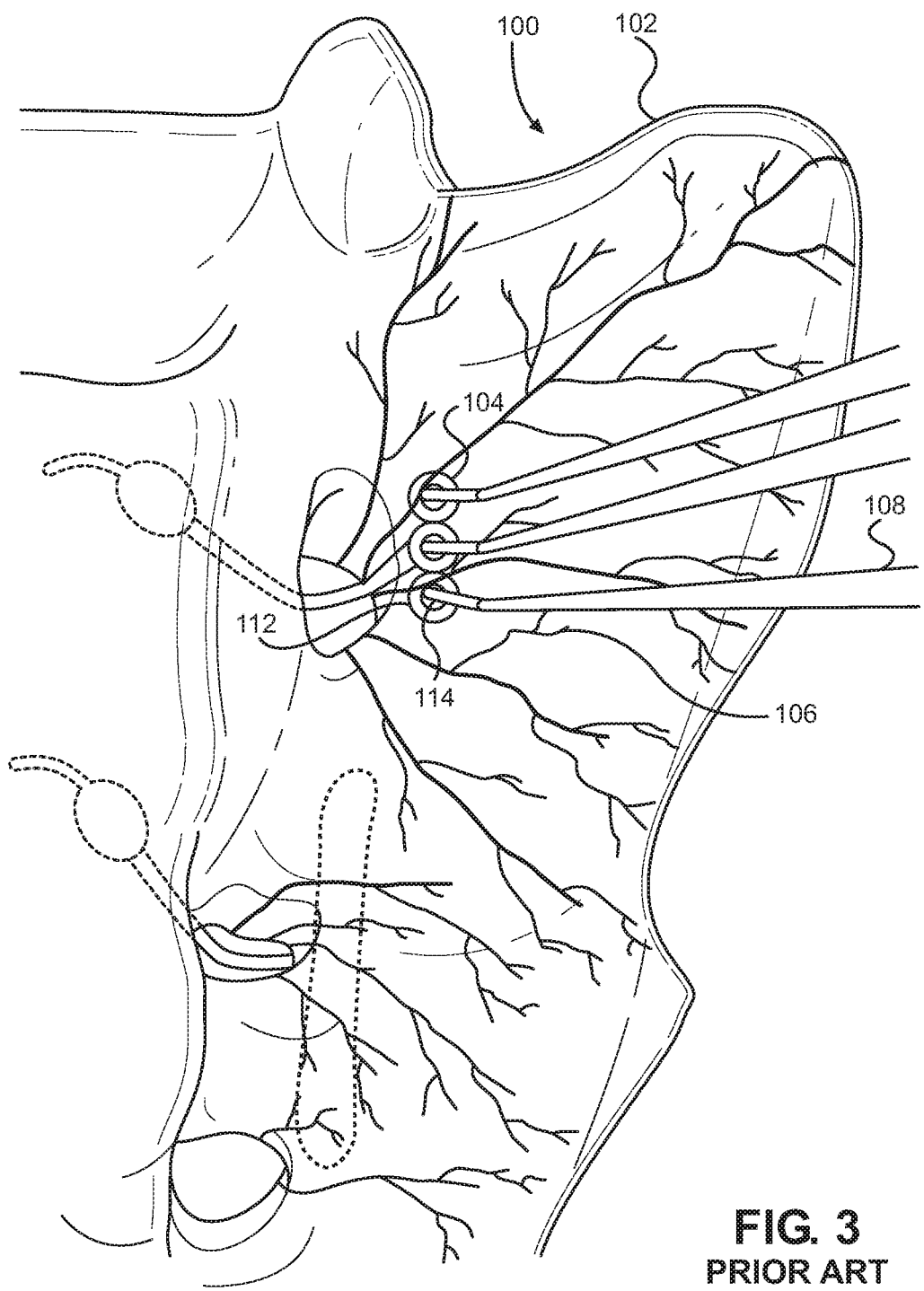
FIG. 3 is a schematic perspective view of the sacrum during radiofrequency denervation according to the prior art.
Figure 4:
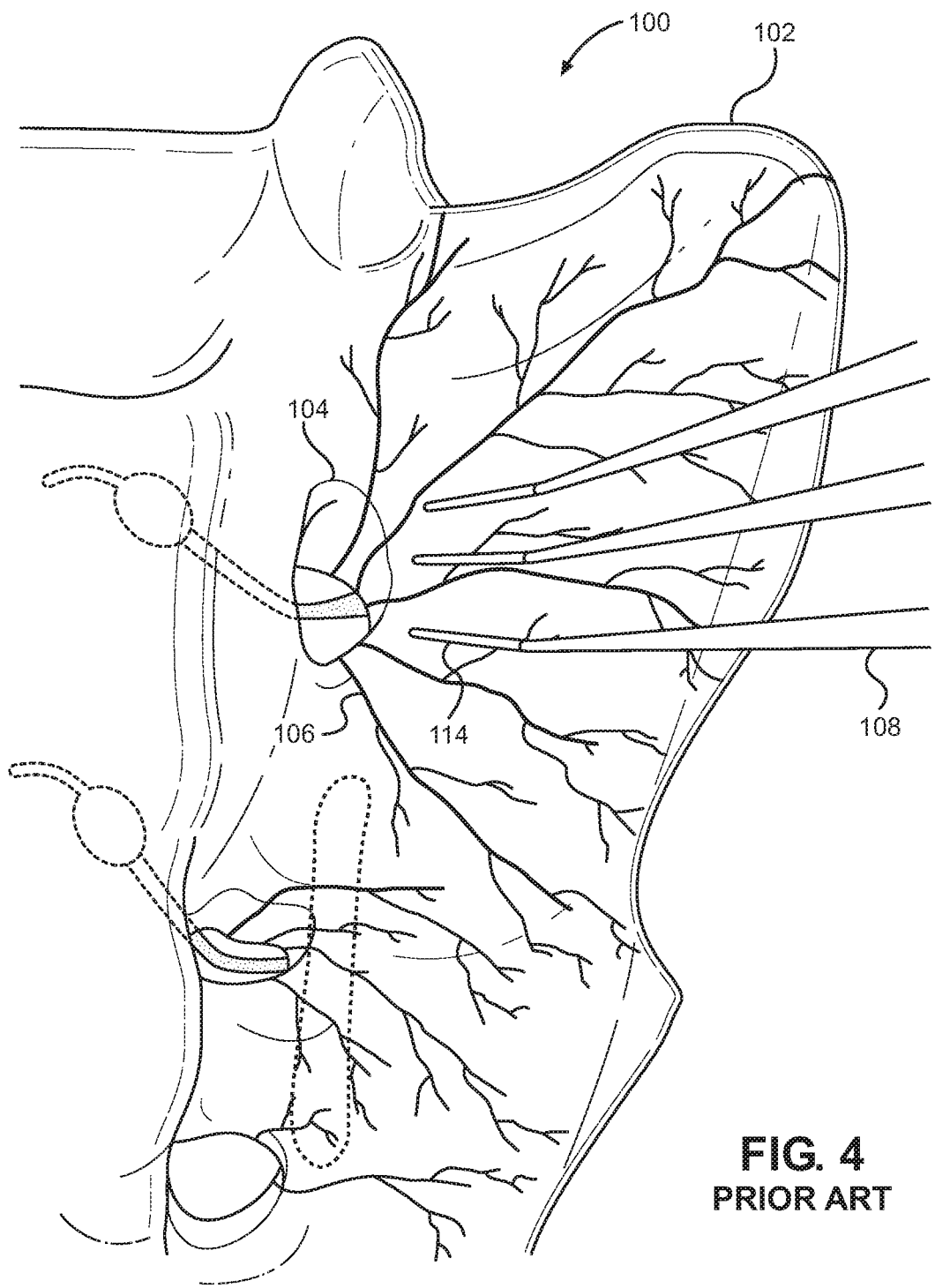
FIG. 4 is a further schematic perspective view of the sacrum during radiofrequency denervation as taught by the prior art.
Figure 5:
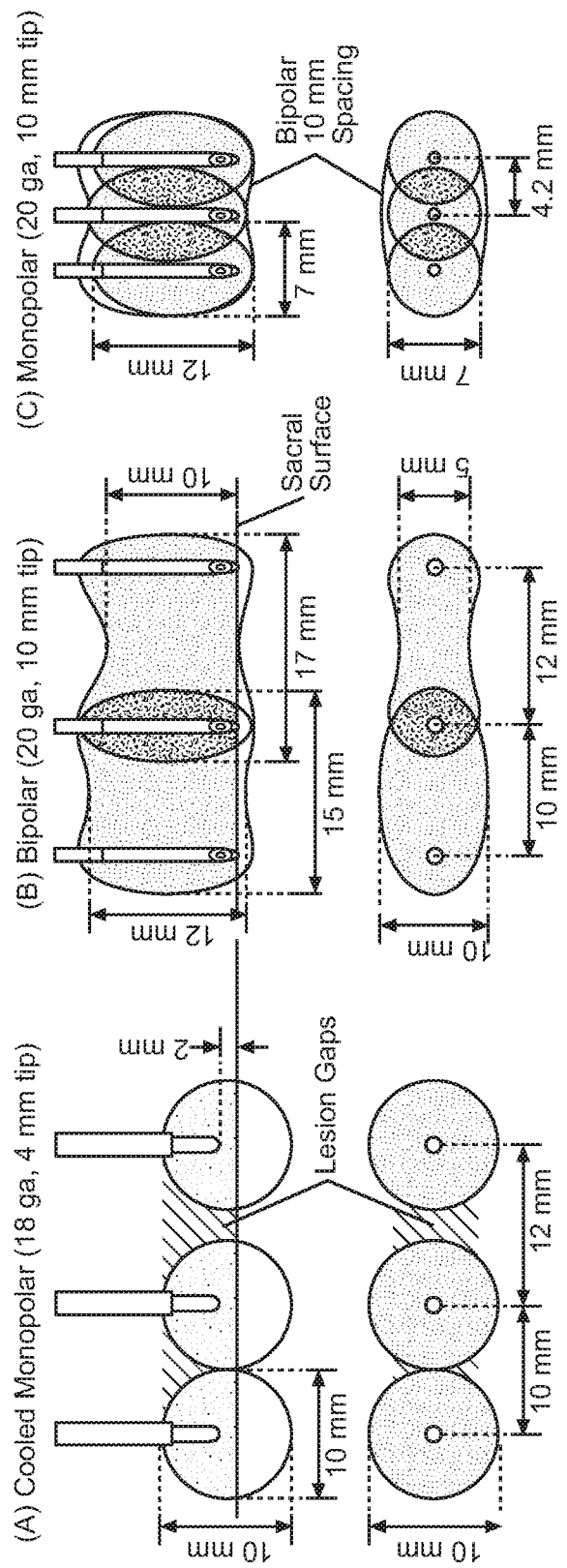
FIG. 5 provides elevational and plan views of lesions formed under various methods of radiofrequency denervation.

The disclosed needle 12 provides effective radiofrequency lesioning of the sacroiliac joint innervation 106 without burning additional tissue in between the foramens 104 that are not involved in the innervation of the sacroiliac joint 120 as seen in FIG. 2, for instance. This targeted lesioning of the lateral aspect of the posterior sacral foramen 104 with only one needle 12 is unique to this design and significantly lessens side effects, such as pain, muscle spasm, decreased physical activity, time from off work, post-operative pain medication, and others, while significantly decreasing the recovery time. The time for the operation can be significantly less in comparison to other radiofrequency methods currently in use. Thus, the financial cost is significantly less compared to other currently used methods for sacroiliac joint denervation. The denervation method can further be used in conjunction with ultrasound techniques.

Spirals within a given needle 12 can have a consistent diameter from the proximal portion to the distal tip, or they can taper, such as generally along a conical shape. Needles 12 can vary in length and pitch depending on the desired end use. Within each individual needle 12, the diameter and the pitch can be consistent, or they could vary.

In one practice of the present method, the procedure can include placing a dispersive return electrode pad 22, shown in FIG. 9, on the patient, such as on one of the lower extremities. The lower back and buttock area are cleaned with an antiseptic solution and draped in a standard, sterile fashion with towels. Using an anteroposterior fluoroscopic view with a slight ipsilateral (20 degrees) oblique tilt, the S1, S2, and S3 posterior sacral foramina apertures 104 are identified. Using the posterior sacral foramina aperture 104 as a "clock-face," a skin marker is used to mark the bony landmark in a semi-circle fashion, just a few millimeters parallel to the lateral aspect of each respective neural foramen 104 as determined by anteroposterior fluoroscopic views (from 12 o'clock to 6 o'clock). These locations serve as reference points for placement of the 20 mm active tip 16 of the needle 12 and its electrode 20 over the bone landmark. One can then identify the 12 o'clock skin projection point of every foramen 104 and infiltrate with 2-3 mL of 1% Lidocaine. The needle tip 14 is inserted in a screw-like motion over the numb area guided by the lateral aspect of the foramen 104 keeping the ring-like image of the helical tip 14 in anteroposterior x-ray view, always around the foramen 104.

A tunnel-view approach can be employed sequentially onto the target positions described above. The practitioner can ensure bone is contacted and the entire length of the semicircular active tip 16 is as close as possible and substantially parallel to the bone surface 102 in the half lateral aspect of the foramen 104. If it is not, the needle 12 can be maneuvered with a gentle clockwise or counter-clockwise movement. Lateral views are taken to ensure proper depth of insertion of the needle as in FIG. 9.

At each of the respective target positions, impedance within the range of 200-500 ohms and baseline temperature readings are obtained. Once the position is verified, 1 mL of 0.25% bupivacaine is injected at each lesion site.

Radiofrequency lesioning is then carried out at a set temperature of, for example, 80 degrees Celsius for 120 seconds. Subsequently, to widen the initial lesion if desired and, potentially, under direct x-ray lateral viewing, a second lesion above the first lesion can be made. The needle 12 with the active tip 16 forming a portion thereof can be repositioned, such as by rotating clockwise or counterclockwise, depending on the orientation of the pitch of the needle 12, 360 degrees. The pitch causes the active tip 16 to relocate above the first position, such as by approximately 10 mm. The operator can then lesion for a second time, if desired. The operator could also rotate the needle clockwise again while manipulating the needle 12, such as with a slight pull and push of the needle 12 to locate the active tip 16 approximately 4-5 mm above the first lesion. The radiofrequency protocol referenced above can be repeated with each desired positioning.

Such a method can add 4-6 mm more length to the initial lesion and will denervate additional nerve branches 106 that might be taking off from the lateral aspect of the posterior sacral foramen 104 that are, for instance, traveling just above the bony surface 102. While such nerves 106 could be missed during initial lesioning, a greater area of tissue lateral to the posterior sacral foramina 104 will ultimately be lesioned, and the chances for a successful ablation and denervation of the SI joint 120 is achieved. The lesioning is done along the lateral aspect of the S1 as well as lesions lateral to the S2 and S3 posterior sacral foraminal apertures 104 of the painful joint 120.

The respective location of the left or right dorsal rami of L5 over the sacral ala is identified using an oblique fluoroscopic view. Sensory stimulation is obtained at less than 0.5 V and 50 Hz and motor stimulation at 2 Hz negative up to 1.5 V. The L5 dorsal ramus is then lesioned, such as at 80 degrees celsius for 120 seconds.

It will be understood that other embodiments of the radiofrequency denervation device 10 are within the scope of the invention. By way of example, an alternative radiofrequency denervation device is again depicted generally at 10 in FIGS. 11 through 15 where the radiofrequency denervation device 10 is again shown during the process of radiofrequency denervation of the sacriliac joint of a patient. A radiofrequency cannula or needle 12 of the device 10 has a proximal portion and a distal portion. A handle 18 is disposed at the proximal portion of an elongate body portion of the needle 12, and the needle 12 can selectively engage with an electrode 20. The tip 14 of the needle 12 has a radiofrequency active area 16 capable of producing lesions in surrounding volumes of tissue when rendered electrically active by operation of the electrode 20 and a non-conductive or inactive area 24 proximal to the active area 16.

The active area 16 again has a portion thereof having an arcuate formation generally concentric with a longitudinal axis A of the needle 12. The arcuate formation of the active area 16 of the tip 14 communicates over an arcuate path over a longitudinal dimension and a lateral dimension relative to the needle 12. The active area 16 of the tip 14 again follows a helical pattern. While in the embodiment of FIG. 6, for instance, the tip 14 followed a helical pattern with plural revolutions, the tip 14 in the embodiment of FIGS. 11 through 15 just approximately one revolution. As before, the helical pattern of the tip 14 could be generally consistent in effective diameter, or it could taper in effective diameter toward the distal end thereof.

The active area 16 of the tip 14 travels over an arcuate pattern with a given pitch relative to the body portion of the needle 12 thereby travelling along an arcuate path over a longitudinal dimension and a lateral dimension. The helical active area 16 traverses an arcuate, helical pattern with an angle of attack relative to the longitudinal axis of the needle 12 so that the tip 14 can enter and travel through the tissue of a patient in a screw pattern, potentially along the angle of attack, with the active tip portion 16 having a substantial lateral dimension, a longitudinal dimension, and a curvature. By use of the method of denervation described hereinabove, volumes of tissue lesioned by the active tip portion 16 of the tip 14 will similarly tend to have a substantial lateral dimension, a longitudinal dimension, and, potentially, a curvature. Here, the active tip 16 spans approximately 180 degrees of a revolution of the spiral and again forms the most distal portion of the needle 12.

Figure 13:
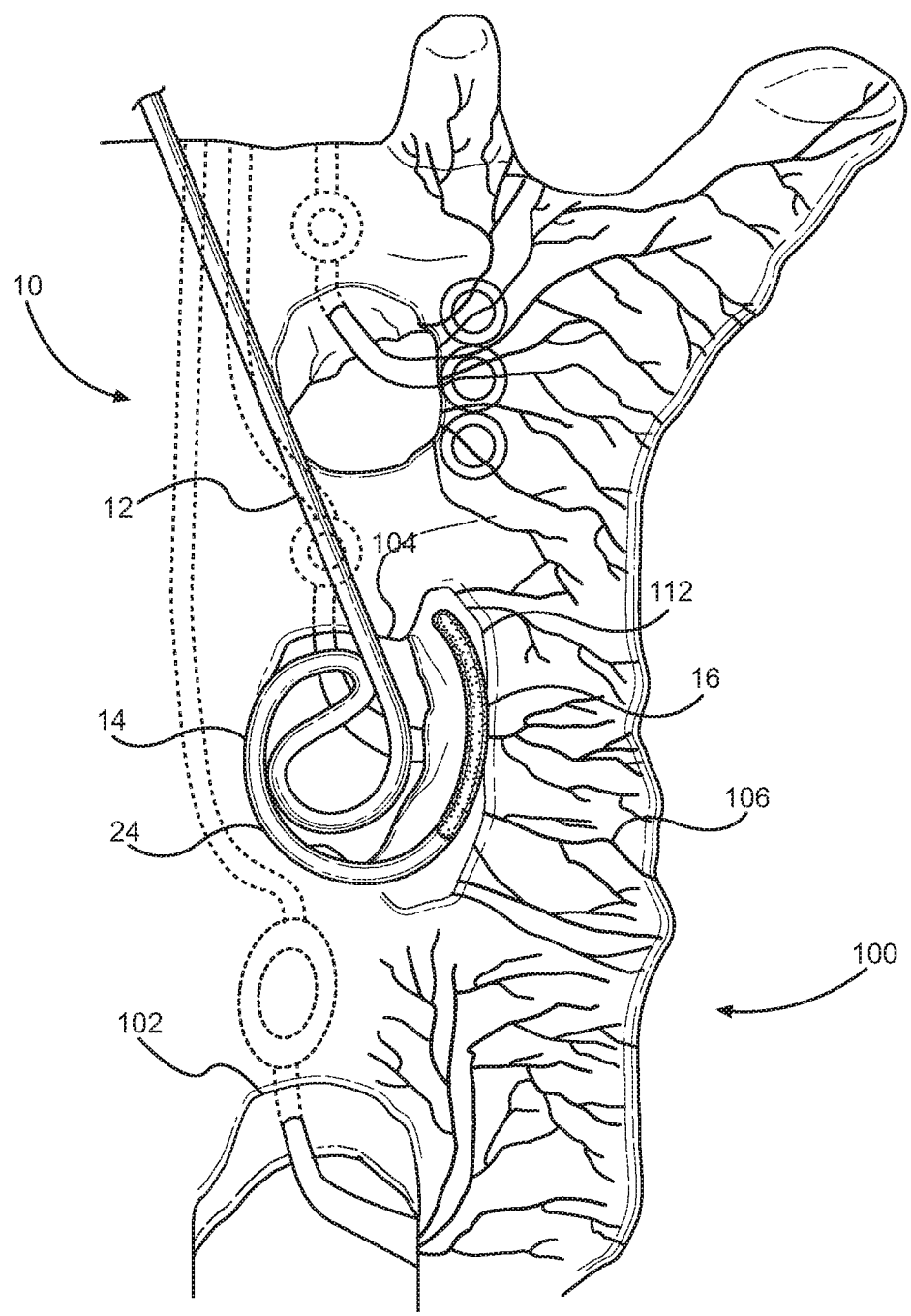
FIG. 13 is a further perspective view of a radiofrequency denervation device pursuant to the invention during a process of denervation of the sacroiliac joint.
Figure 14:
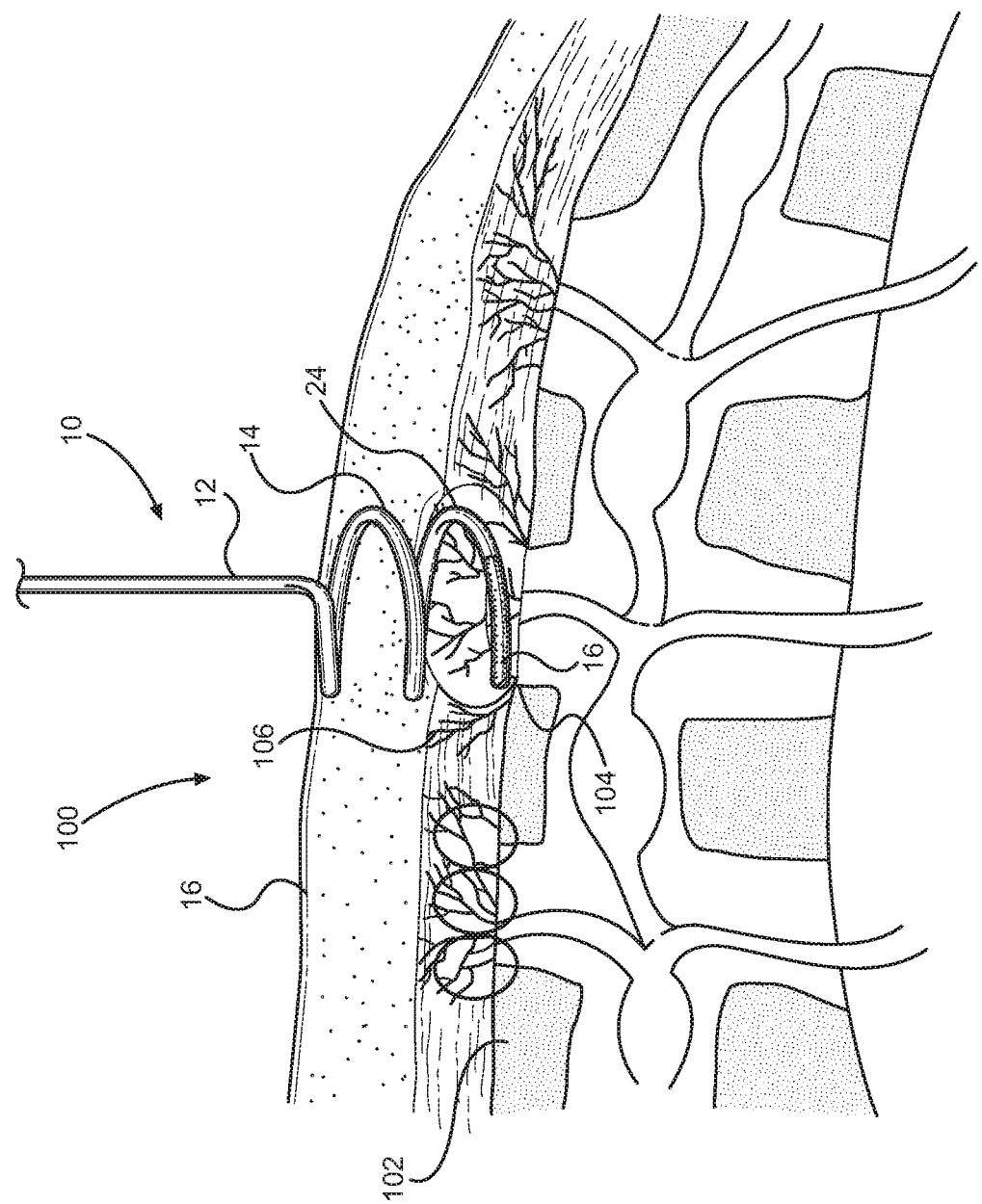
FIG. 14 is a lateral view of a radiofrequency denervation device according to the present invention in a first position during a process of denervation of the sacroiliac joint.
Figure 15:
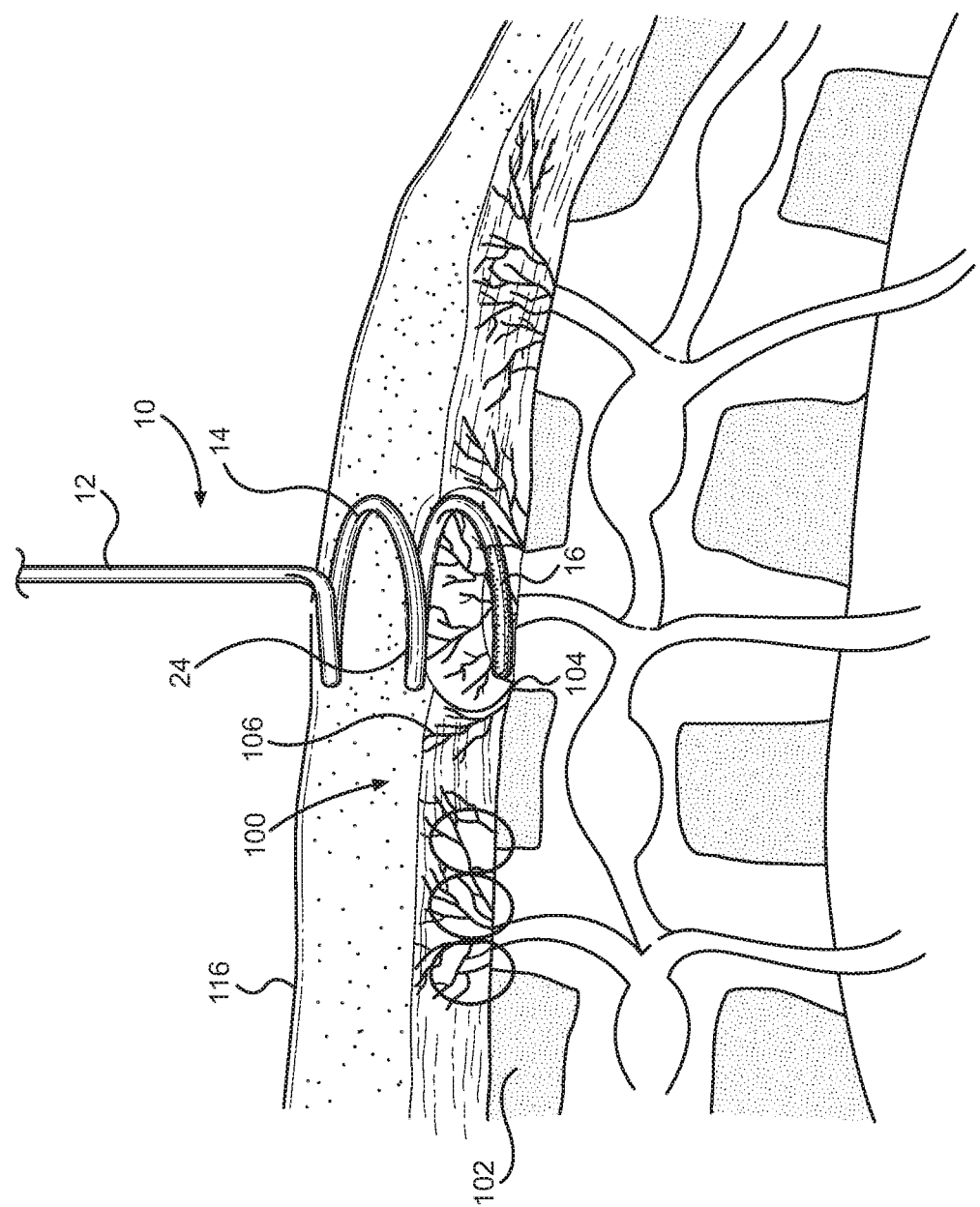
FIG. 15 is a lateral view of the radiofrequency denervation device of FIG. 14 in a second position during a process of denervation of the sacroiliac joint.

The active tip 16 can be selectively placed relative to the sacrum 102 or another area of the body, such as by being disposed to traverse a semicircular pattern spaced, for instance, just a few millimeters parallel to the lateral aspect of the posterior sacral foramen 104 over the bony surface of the sacrum 102. When the tip 16 is activated, radiofrequency heating can effectively denervate the majority, if not all, the sensory branches 106 that leave the foramen 104 over the level of the active tip 16. As seen in FIG. 13, for example, the arcuate active tip 16 positioned substantially parallel to the lateral aspect of the posterior sacral foramen 104 will thus tend to produce a lesion 112 traversing a substantial lateral, arcuate dimension thereby providing a high likelihood of effective denervation of nerves 106 spaced over a given area.

Once an initial placement and lesioning is done, the needle 12 can be rotated to adjust the position of the active tip 16, if necessary, potentially with guidance through a lateral x-ray view. Rotation of the needle 12 over 360 degrees will cause the active tip 16 to be positioned above the previous lesioning. Further positioning could be carried out as necessary to produce effective denervation.

It should be noted that certain elements in some of the figures may be omitted, or illustrated not-to-scale. For illustrative clarity, the cross-sectional views may be in the form of slices or near-sighted cross-sectional views, potentially omitting certain background portions that would otherwise be visible in a true cross-sectional view. In the drawings, both references numerals and legends may be used to identify elements. If legends are provided, they are intended merely as an aid to the reader, and should not in any way be interpreted as limiting.

It will thus be appreciated that the radiofrequency needle device 10 can lead to larger, more effectively oriented and controlled lesions. By treating a greater area of tissue lateral to the posterior sacral foramina 104, the radiofrequency method and system increase the chance of disrupting the sacral lateral branches 106 successfully. The involved method can use a single, disposable radiofrequency probe needle 12 to enlarge lesion size in the precise target area without burning tissue that is not involved in the denervation of the sacroiliac joint 120. The design of the needle 12 allows the operator to place the active tip 16 safely and easily substantially parallel to the bone 102 in front of the lateral aspect of the sacral foramen 104 in a semicircular manner. This maximizes the chance of complete denervation of the sacroiliac joint 120. There are many benefits to the disclosed method over existing methods for the best chance of a successful denervation of the sacroiliac joint 120.

With certain details and embodiments of the present invention for a radiofrequency needle 10 and method for radiofrequency denervation disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein. Accordingly, it will be clear that those with major features of the invention in mind could craft embodiments that incorporate those major features while not incorporating all of the features included in the preferred embodiments.

Therefore, the following claims shall define the scope of protection to be afforded to the inventor. Those claims shall be deemed to include equivalent constructions insofar as they do not depart from the spirit and scope of the invention. It must be further noted that a plurality of the following claims may express, or be interpreted to express, certain elements as means for performing a specific function, at times without the recital of structure or material. As the law demands, any such claims shall be construed to cover not only the corresponding structure and material expressly described in this specification but also all equivalents thereof.

What is claimed as deserving the protection of Letters Patent:

1. A percutaneous method of radiofrequency denervation within tissue of a human patient in proximity to a lateral aspect of a posterior sacral foramen of a sacrum, the percutaneous method comprising the following steps:
   providing a radiofrequency denervation device comprising a needle with a proximal portion, a distal portion, and a longitudinal axis; and an elongate electrode for engaging the needle,
   wherein the needle has a tip with an inactive portion and a radiofrequency active portion capable of producing lesions in surrounding volumes of tissue when rendered active by operation of the elongate electrode;
   a distal portion of the inactive portion of the tip of the needle and the radiofrequency active portion of the tip of the needle are disposed in a helical formation;
   the helical formation of the active portion communicates over an arcuate path along the tip of the needle over an angular range of a helical revolution with an angle of attack relative to the longitudinal axis of the needle with a longitudinal dimension and a lateral dimension; and
   the helical formation of the active portion of the tip of the needle is generally concentric with the longitudinal axis of the needle;
   identifying posterior sacral foramina apertures within the patient;
   percutaneously inserting the tip of the needle into tissue of the patient to cause the tip of the needle to enter and travel through the tissue of the patient in a screw pattern comprising rotating the tip of the needle in a screw-like motion in a first rotational direction to achieve a first tip position within the tissue of the patient in proximity to the human sacrum with the radiofrequency active portion of the tip communicating laterally across the lateral aspect of the posterior sacral foramen traversing a semicircular pattern;
   inserting the elongate electrode into the needle;
   actuating the active portion of the tip with the elongate electrode to a temperature sufficient to produce radiofrequency lesioning to produce a lesion in the tissue of the patient in proximity to the human sacrum and to denervate nerve branches in proximity to the lateral aspect of the posterior sacral foramen.

2. The percutaneous method of claim 1, wherein the step of inserting the tip of the needle into the tissue of the patient comprises inserting the tip of the needle into tissue in proximity to the human sacrum with the active portion of the tip substantially parallel to a surface of the sacrum by rotating the tip of the needle in a screw-like motion in the first rotational direction to cause the tip to navigate through the tissue of the patient in the screw pattern.

3. The percutaneous method of claim 2, wherein the step of inserting the tip of the needle into tissue in proximity to the human sacrum comprises inserting the tip of the needle into tissue in proximity to the human sacrum with the active portion of the tip substantially parallel to the lateral aspect of the posterior sacral foramen.

4. The percutaneous method of claim 2, wherein the step of inserting the tip of the needle into the tissue of the patient includes contacting bone of the sacrum with the tip of the needle.

5. The percutaneous method of claim 1, further comprising repositioning the tip of the needle to a second tip position within the tissue of the patient and actuating the active portion of the tip to produce a second lesion in the tissue of the patient wherein the step of repositioning the tip of the needle comprises rotating the tip of the needle in a second rotational direction opposite the first rotational direction to achieve the second tip position.

6. The percutaneous method of claim 5, wherein the step of repositioning the tip of the needle comprises rotating the tip of the needle in a second rotational direction by approximately 360 degrees so that the second tip position is above the first tip position.

7. The percutaneous method of claim 1, wherein the step of actuating the active portion of the tip to produce a lesion in the tissue of the patient comprises delivering radiofrequency energy from the electrode to the active portion of the tip.

8. The percutaneous method of claim 1, wherein the radiofrequency active portion spans an arcuate path along the tip of approximately 180 degrees of a helical revolution.

9. The percutaneous method of claim 1, wherein the needle has a tip with one radiofrequency active portion.

10. The percutaneous method of claim 9, wherein the one radiofrequency active portion spans an arcuate path along the tip of between approximately 90 degrees and approximately 360 degrees of a helical revolution.

11. The percutaneous method of claim 10, wherein the radiofrequency active portion spans an arcuate path along the tip of approximately 180 degrees of a helical revolution.

* * * * *